(12) United States Patent
Sjong et al.

(10) Patent No.: US 9,994,597 B2
(45) Date of Patent: Jun. 12, 2018

(54) INORGANIC SILOXANE LADDER COMPOSITES AND METHODS OF THEIR PREPARATION

(71) Applicant: EMPIRE TECHNOLOGY DEVELOPMENT LLC, Wilmington, DE (US)

(72) Inventors: Angele Sjong, Louisville, CO (US); Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days. days.

(21) Appl. No.: 15/306,471

(22) PCT Filed: Apr. 24, 2014

(86) PCT No.: PCT/US2014/035316
§ 371 (c)(1),
(2) Date: Oct. 24, 2016

(87) PCT Pub. No.: WO2015/163890
PCT Pub. Date: Oct. 29, 2015

(65) Prior Publication Data
US 2017/0044190 A1  Feb. 16, 2017

(51) Int. Cl.
| | | |
|---|---|---|
| *C07F 7/00* | (2006.01) | |
| *C07F 7/08* | (2006.01) | |
| *C07C 211/63* | (2006.01) | |
| *C07F 7/28* | (2006.01) | |
| *C08G 83/00* | (2006.01) | |
| *G02B 6/122* | (2006.01) | |
| *G02B 6/12* | (2006.01) | |

(52) U.S. Cl.
CPC ............ *C07F 7/085* (2013.01); *C07C 211/63* (2013.01); *C07F 7/006* (2013.01); *C07F 7/0841* (2013.01); *C07F 7/0843* (2013.01); *C07F 7/28* (2013.01); *C08G 83/001* (2013.01); *G02B 6/122* (2013.01); *G02B 2006/1219* (2013.01); *G02B 2006/12038* (2013.01)

(58) Field of Classification Search
CPC ........ C07F 7/085; C07F 7/006; C07F 7/0841; C07F 7/0843; C07F 7/28; C07C 211/63; C08G 83/001; G02B 6/122

USPC .......................................................... 556/439
See application file for complete search history.

(56) References Cited

U.S. PATENT DOCUMENTS

| | | | |
|---|---|---|---|
| 5,230,962 A * | 7/1993 | Stephenson ............... | C08F 8/30 106/287.1 |
| 5,922,527 A | 7/1999 | Barlow et al. | |
| 6,737,370 B2 | 5/2004 | Espe | |
| 7,288,144 B2 | 10/2007 | Uozumi et al. | |
| 2007/0248537 A1 | 10/2007 | Yang et al. | |
| 2011/0165459 A1 | 7/2011 | Halalay et al. | |

FOREIGN PATENT DOCUMENTS

WO   2008071850 A2   6/2008

OTHER PUBLICATIONS

Fonari et. al., Crown-templated assembling of the inorganic binuclear fluoro-containing anions in the system ZrO2/HfO2 (Nb2O5/Ta2O5)-HF-H2O-azacrown ether, Polyhedron (Jun. 2008), 27(9) pp. 2049-2058.
International Search Report and Written Opinion for International Application No. PCT/US2014/035316, dated Aug. 28, 2014, pp. 8.
Lee et al., Refractive index engineering of transparent ZrO2—polydimethylsiloxane nanocomposites, Journal of Material Chemistry (2008), (18) pp. 1751-1755.
Zhang et. al., High refractive index inorganic-organic interpenetrating polymer network (IPN) hydrogel nanocomposite toward artificial cornea implants, ACS Macro Letters (Jun. 2012), 1(7) pp. 876-881.

\* cited by examiner

*Primary Examiner* — Sudhakar Katakam
*Assistant Examiner* — Kofi Adzamli
(74) *Attorney, Agent, or Firm* — Pepper Hamilton LLP

(57) ABSTRACT

Inorganic siloxane ladder polymers with metal-aza/thio crown complexes, and methods of making and using such siloxane ladder polymers are disclosed. The polymers described herein may exhibit self-healing properties, a low dielectric constant, and a low refractive index. These siloxane ladder polymers are anchored to transparent, high-refractive index (RI) metal nanoparticles, such as $ZrO_2$, via aza/thio crown macromolecules. The siloxane ladder polymers may be considered as "living polymer network" since the polymer active chain ends may further undergo anionic polymerization.

21 Claims, 1 Drawing Sheet

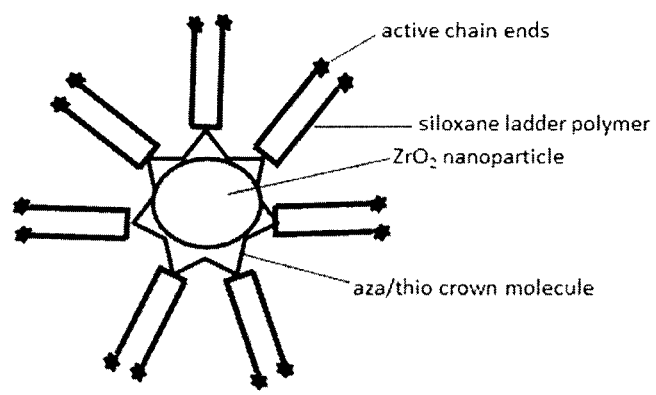

INORGANIC SILOXANE LADDER COMPOSITES AND METHODS OF THEIR PREPARATION

CROSS-REFERENCE TO RELATED APPLICATION

This application is a U.S. national stage filing under 35 U.S.C. § 371 of International Application No. PCT/US2014/035316 filed on Apr. 24, 2016 entitled "INORGANIC SILOXANE LADDER COMPOSITES AND METHODS OF THEIR PREPARATION," which is incorporated herein by reference in its entirety.

BACKGROUND

The demand for a continuous increase in transmission speed, data capacity and data density in integrated optical and optoelectronic circuits has been the motivating force behind numerous innovations in areas of broadband communications, high-capacity information storage, large screen and portable information display, and other areas. Although glass optical fibers are routinely used for high-speed data transfer over long distances, they are inconvenient for complex high-density circuitry because of their high density, poor durability, and high cost of fabrication for complex photonic circuits. Thus, there is a need to develop alternative materials that can at least ameliorate or address the aforementioned problems. Such materials can be any one or more of stable during phase transitions (for example, crystallization or melting), chemically stable, and stable in terms of optical loss, index of refraction, and/or density.

SUMMARY

This disclosure is related to compositions of fluorinated siloxanes with metal-aza crown and/or metal-thio crown complexes, and methods of making and their use. One embodiment provides a compound of formula I:

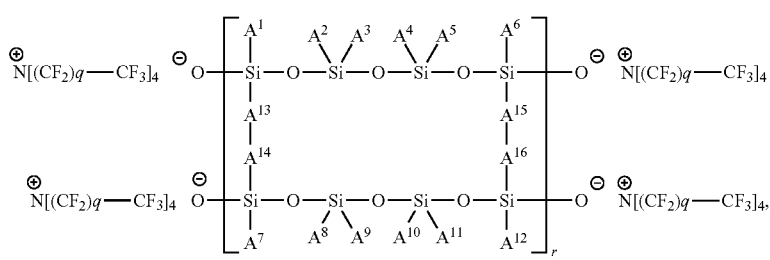

wherein q is an integer from 1 to 3;

r is an integer from 1 to 10000;

each $A^1$, $A^2$, $A^3$, $A^4$, $A^5$, $A^6$, $A^7$, $A^8$, $A^9$, $A^{10}$, $A^{11}$, and $A^{12}$ independently is, —$CF_3$, —$CH_3$, —$CF_2$—C(=O)—F, —$C_6F_5$, —CF=$CF_2$, —$CF_2$—CF=$CF_2$, a metal-aza crown complex, a metal-thio crown complex, or a metal-acrylic acid complex, and wherein at least one of $A^1$, $A^2$, $A^3$, $A^4$, $A^5$, $A^6$, $A^7$, $A^8$, $A^9$, $A^{10}$, $A^{11}$, and $A^{12}$ is a metal-aza crown complex or a metal-thio crown complex; and each $A^{13}$, $A^{14}$, $A^{15}$, and $A^{16}$ independently is —$CH_2$— or —$CF_2$—.

Another embodiment provides a compound of formula IV:

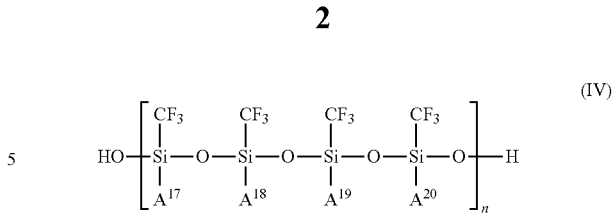

wherein n is an integer from 1 to 100;

$A^{17}$ is a metal-aza crown complex or a metal-thio crown complex;

$A^{18}$ is a metal-aza crown complex or a metal-thio crown complex;

$A^{19}$ is a metal-aza crown complex or a metal-thio crown complex; and $A^{20}$ is a metal-aza crown complex or a metal-thio crown complex.

Another embodiment provides a compound of formula V:

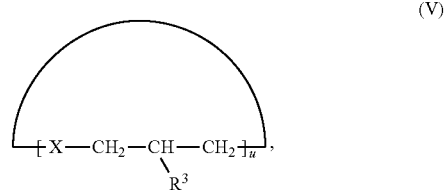

wherein X is —NH— or —S—;

u is an integer from 4 to 12; and each $R^3$ is, independently, —H, —F, —Cl, —$CF_3$, —OH, —$CF_2Cl$, —$CH_2Cl$, —COCl, or —$NH_2$.

A further embodiment provides a compound of formula VI:

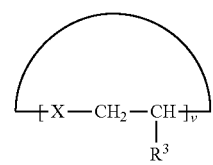

wherein X is —NH— or —S—;

v is an integer from 4 to 12; and each $R^3$ is, independently, —H, —F, —Cl, —$CF_3$, —OH, —$CF_2Cl$, —$CH_2Cl$, —COCl, or —$NH_2$.

In an additional embodiment, an article or a polymer may include one or more compounds of formulae I, IV, V, or VI as described herein. In another embodiment, an optical waveguide structure may include a light transmitting core material having a first refractive index, and a cladding material contacting partially or entirely surrounding the core material, wherein the cladding material has a second refractive index lower than the first refractive index of the core material, and wherein the core material may include one or more compounds of formulae I, IV, V, or VI as described herein.

In a further embodiment, a method of making a siloxane compound of formula I may involve contacting a metal-crown complex with trifluorochloromethane and a silicon metal to form a dichlorosilane-metal-crown complex, hydrolyzing the dichlorosilane-metal-crown complex to form a fluorinated siloxane polymer compound of formula IV, and contacting the polymer compound of formula IV with a bis-siloxane D4 compound and an anionic catalyst to form the siloxane compound of formula I.

BRIEF DESCRIPTION OF THE FIGURES

FIG. 1 depicts a string of siloxane ladder polymers attached to a metal-crown complex according to an embodiment.

DETAILED DESCRIPTION

This disclosure is not limited to the particular systems, devices and methods described, as these may vary. The terminology used in the description is for the purpose of describing the particular versions or embodiments only, and is not intended to limit the scope.

A "core material" refers to any layer of an optical waveguide that transmits light. A "cladding material" refers to any layer of an optical waveguide that confines light. In an embodiment, a core layer may be at least partially encompassed by a cladding layer.

A "waveguide" refers to a system having a material that provides a path to guide an electromagnetic wave. A waveguide may have, for example and without limitation, a circular or a rectangular shape.

A "substituted" moiety indicates that any hydrogen on the designated moiety can be replaced with a fluorine group. For example, substituted —$CH_3$ may refer to —$CH_2F$, —$CHF_2$, —$CF_3$, and the like. Similarly, substituted —$CH_2$—C(=O)—H may refer to —$CH_2$—C(=O)—F, —$CF_2$—C(=O)—H, —$CF_2$—C(=O)—F, and the like.

Disclosed herein are inorganic siloxane ladder composites that include metal-aza crown and/or metal-thio crown complexes. These inorganic siloxane ladder polymers are anchored to transparent, high-refractive index (RI) metal nanoparticles, such as $ZrO_2$, via aza/thio crown macromolecules. The siloxane ladder polymers, for example as shown in FIG. 1, may be considered as a "living polymer network" since the polymer active chain ends may further undergo anionic polymerization.

In some embodiments, a compound is of formula I:

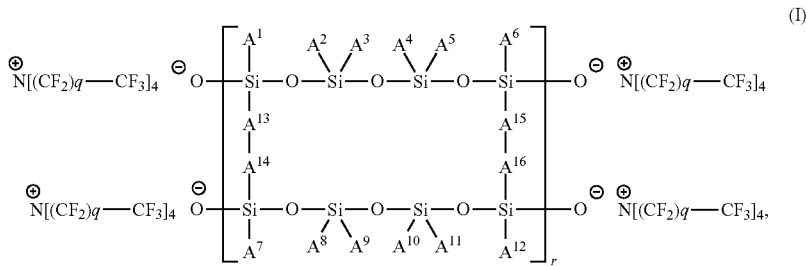

(I)

wherein q is an integer from 1 to 3;
r is an integer from 1 to 10,000;
each $A^1$, $A^2$, $A^3$, $A^4$, $A^5$, $A^6$, $A^7$, $A^8$, $A^9$, $A^{10}$, $A^{11}$, and $A^{12}$ independently is, —$CH_3$, substituted —$CH_3$, —$CH_2$—C(=O)—H, substituted —$CH_2$—C(=O)—H, —$C_6H_5$, substituted —$C_6H_5$, —CH=$CH_2$, substituted —CH=$CH_2$, —$CH_2$—CH=$CH_2$, substituted —$CH_2$—CH=$CH_2$, a metal-aza crown complex, a metal-thio crown complex, or a metal-acrylic acid complex, and wherein at least one of $A^1$, $A^2$, $A^3$, $A^4$, $A^5$, $A^6$, $A^7$, $A^8$, $A^9$, $A^{10}$, $A^{11}$, and $A^{12}$ is a metal-aza crown complex or a metal-thio crown complex; and each $A^{13}$, $A^{14}$, $A^{15}$, and $A^{16}$ independently is —$CH_2$— or —$CF_2$—.

In some embodiments, each $A^1$, $A^2$, $A^3$, $A^4$, $A^5$, $A^6$, $A^7$, $A^8$, $A^9$, $A^{10}$, $A^{11}$, and $A^{12}$ independently may be, —$CH_3$, —$CF_3$, —$CH_2$—C(=O)—H, —$CF_2$—C(=O)—F, —$C_6H_5$, —$C_6F_5$, —CH=$CH_2$, —CF=$CF_2$, —$CH_2$—CH=$CH_2$, —$CF_2$—CF=$CF_2$, a metal-aza crown complex, a metal-thio crown complex, or a metal-acrylic acid complex, and wherein at least one of $A^1$, $A^2$, $A^3$, $A^4$, $A^5$, $A^6$, $A^7$, $A^8$, $A^9$, $A^{10}$, $A^{11}$, and $A^{12}$ is a metal-aza crown complex or a metal-thio crown complex; and each $A^{13}$, $A^{14}$, $A^{15}$, and $A^{16}$ independently may be —$CH_2$— or —$CF_2$—.

In some embodiments, each $A^1$, $A^2$, $A^3$, $A^4$, $A^5$, $A^6$, $A^7$, $A^8$, $A^9$, $A^{10}$, $A^{11}$, and $A^{12}$ independently may be, —$CHF_2$, —$CH_2$—C(=O)—F, —$C_6H_4F$, —CH=$CF_2$, —$CH_2$—CH=$CF_2$, a metal-aza crown complex, a metal-thio crown complex, or a metal-acrylic acid complex, and wherein at least one of $A^1$, $A^2$, $A^3$, $A^4$, $A^5$, $A^6$, $A^7$, $A^8$, $A^9$, $A^{10}$, $A^{11}$, and $A^{12}$ is a metal-aza crown complex or a metal-thio crown complex; and each $A^{13}$, $A^{14}$, $A^{15}$, and $A^{16}$ independently may be —$CH_2$— or —$CF_2$—.

In some embodiments, the compound of formula I may include at least one metal-aza crown complex, at least 10 metal-aza crown complexes, at least 50 metal-aza crown complexes, at least 100 metal-aza crown complexes, at least 500 metal-aza crown complexes, at least 1000 metal-aza crown complexes, at least 5000 metal-aza crown complexes, or at least 10,000 metal-aza crown complexes.

In some embodiments, the compound of formula I may include at least one metal-thio crown complex, at least 10 metal-thio crown complexes, at least 50 metal-thio crown complexes, at least 100 metal-thio crown complexes, at least 500 metal-thio crown complexes, at least 1000 metal-thio crown complexes, at least 5000 metal-thio complexes, or at least 10,000 metal-thio crown complexes.

In some embodiments, the compound of formula I may include a combination of numerous metal-thio crown complexes and numerous metal-aza crown complexes.

In some embodiments, the compound of formula I may include at least one metal-acrylic acid complex, at least 10 metal acrylic acid complexes, at least 50 metal-acrylic acid complexes, at least 100 metal-acrylic acid complexes, at least 500 metal-acrylic acid complexes, at least 1000 metal-acrylic acid complexes, at least 5000 metal-acrylic acid complexes, or at least 10,000 metal-acrylic acid complexes. These acrylic acid groups may co-ordinate with metal nanoparticles and help to anchor them with siloxane ladder polymers.

The metal-aza crown complex disclosed herein may include a metallic nanoparticle in contact with the aza crown molecule. Non-limiting examples of metallic nanoparticle include a $ZrO_2$ nanoparticle, a $TiO_2$ nanoparticle, a ZnS nanoparticle, a ZnO nanoparticle, or any combination thereof. The aza crown molecule may be represented by formula IIa or IIb:

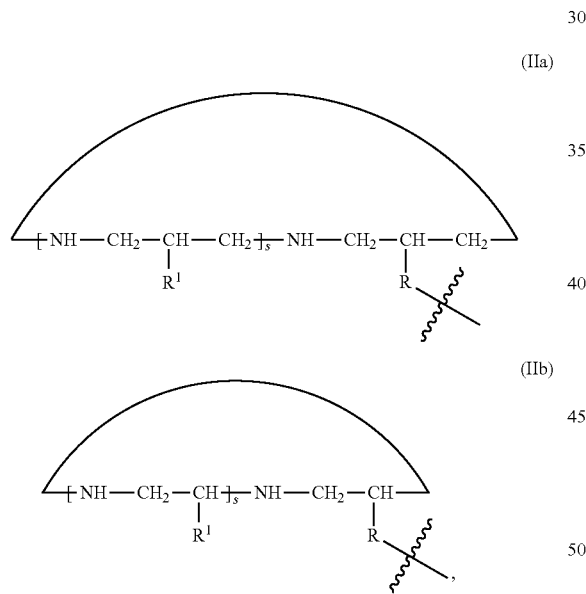

wherein s is an integer from 3 to 12; each R is independently, —O—, —$CF_2$—, —C(=O)—O—, —C(=O)—NH—, or —NH—; and each $R^1$ is independently, —H, —F, —$CF_3$, —OH, —$CF_2Cl$, —$NH_2$. In some embodiments, each $R^1$ may cross-link to another siloxane backbone of formula I, and can be a bivalent —O— linked to the siloxane polymer of formula I, a bivalent —$CF_2$— linked to the siloxane polymer of formula I, or a bivalent —NH— linked to the siloxane polymer of formula I.

In some embodiments, the metal-aza crown complex of formula IIa or IIb may be:

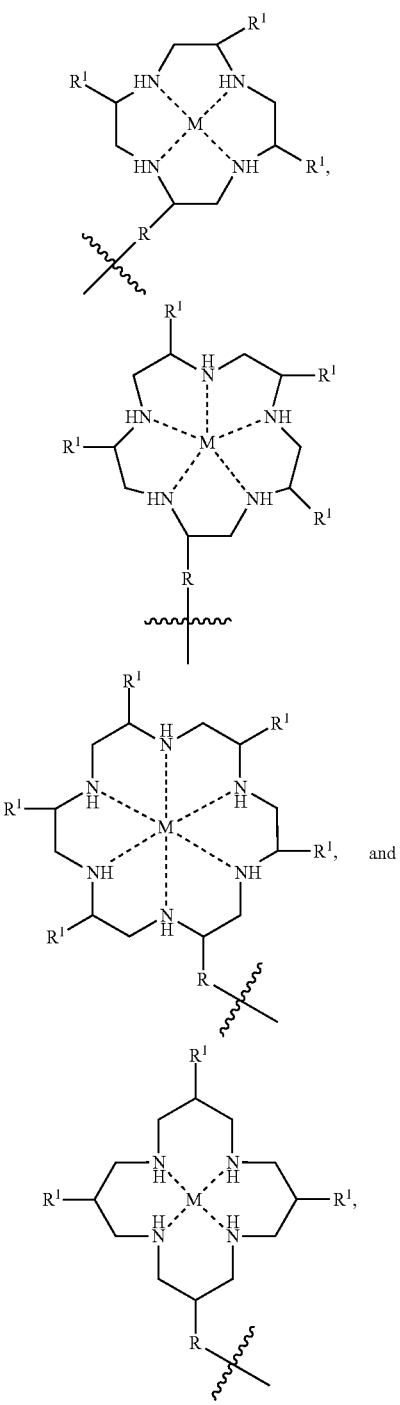

wherein M is $ZrO_2$ nanoparticle, $TiO_2$ nanoparticle, ZnS nanoparticle, or ZnO nanoparticle; R is —O—, —$CF_2$—, —C(=O)—O—, —C(=O)—NH—, or —NH—; and each $R^1$ is independently, —H, —F, —$CF_3$, —OH, —$CF_2Cl$, —$NH_2$, a bivalent —O— linked to the siloxane polymer of formula I, a bivalent —$CF_2$— linked to the siloxane polymer of formula I, or a bivalent —NH— linked to the siloxane polymer of formula I.

Non-limiting examples of the metal-aza crown complex molecules attached to the siloxane polymer of formula I are shown below:

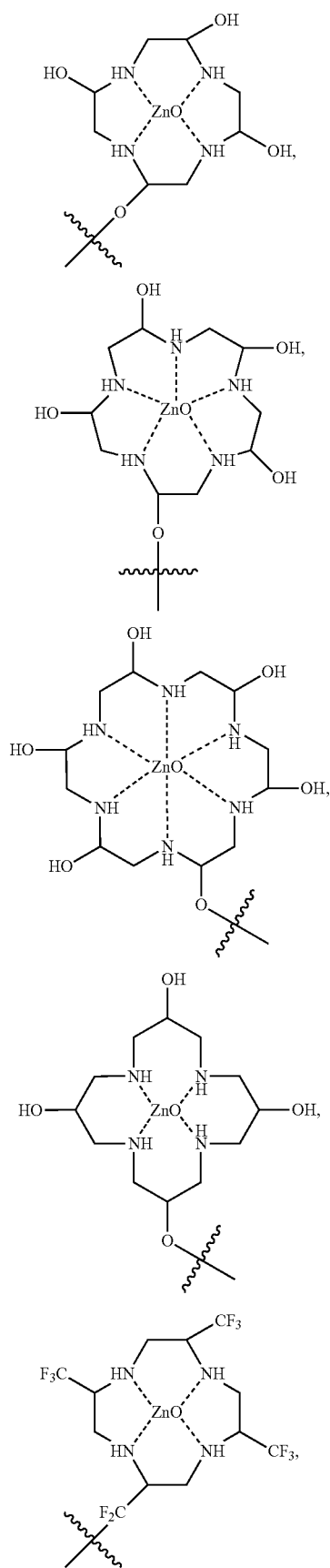

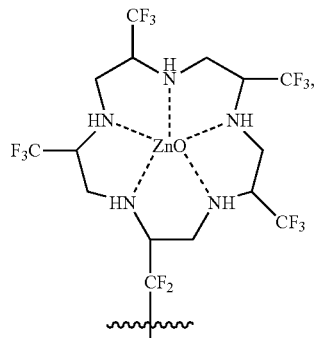

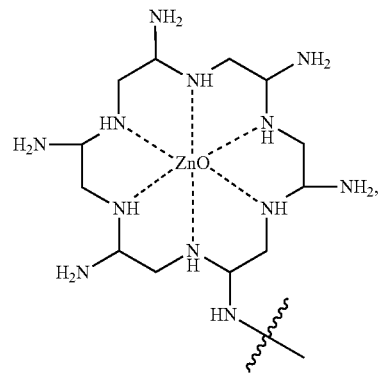

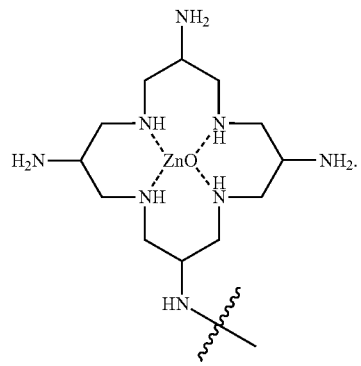

In some embodiments, the metal-thio crown complex disclosed herein may include a metallic nanoparticle in contact with the thio crown molecule. Non-limiting examples of metallic nanoparticle include a $ZrO_2$ nanoparticle, a $TiO_2$ nanoparticle, a ZnS nanoparticle, a ZnO nanoparticle, or any combination thereof. The thio crown molecule may be represented by formula IIIa or IIIb:

(IIIa)

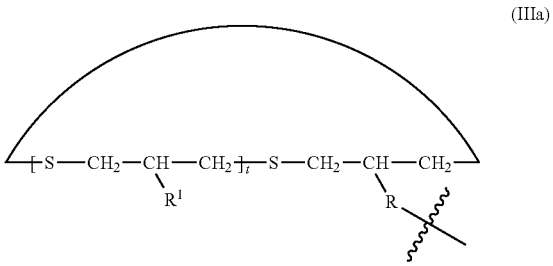

(IIIb)

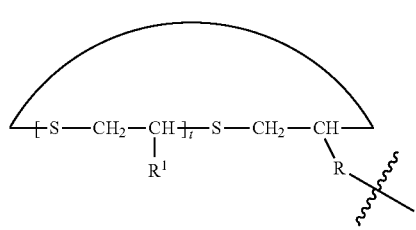

wherein t is an integer from 3 to 12; each R is, independently, —O—, —CF$_2$—, —C(=O)—O—, —C(=O)—NH—, or —NH—; and each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

In some embodiments, the metal-thio crown complex of formula IIIa or IIIb may be:

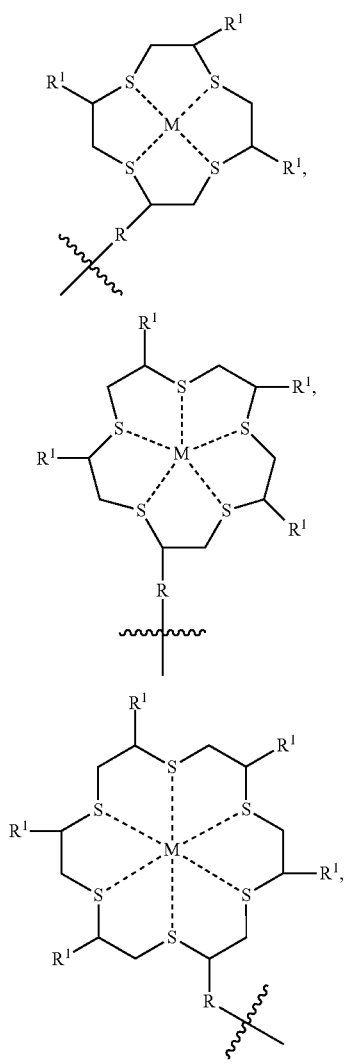

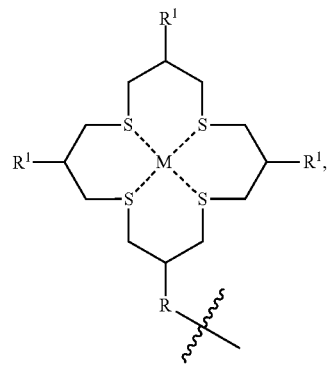

wherein M is ZrO$_2$ nanoparticle, TiO$_2$ nanoparticle, ZnS nanoparticle, or ZnO nanoparticle; R is, independently, —O—, —CF$_2$—, —C(=O)—O—, —C(=O)—NH—, or —NH—; and each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

Non-limiting examples of the metal-thio crown complex molecules attached to the siloxane polymer of formula I are shown below:

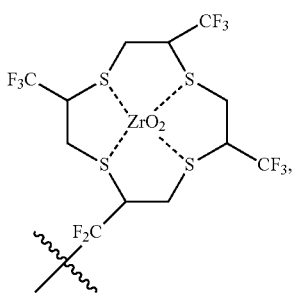

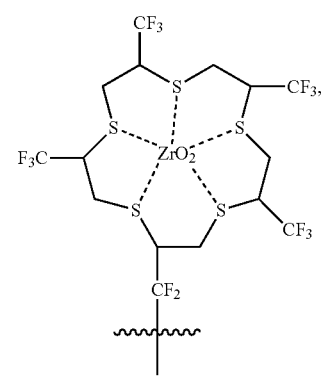

-continued
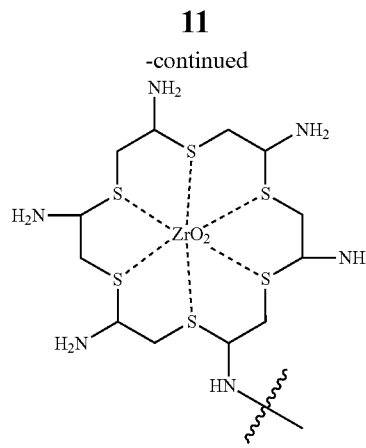
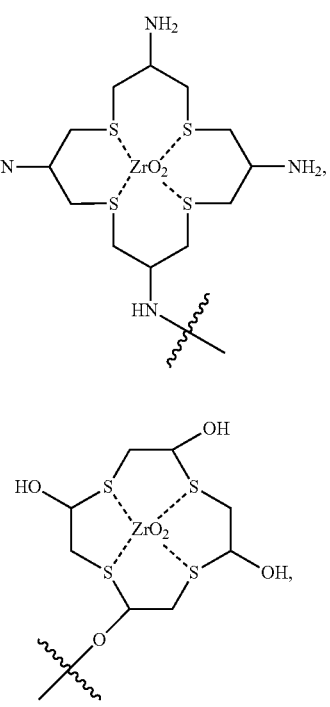
-continued
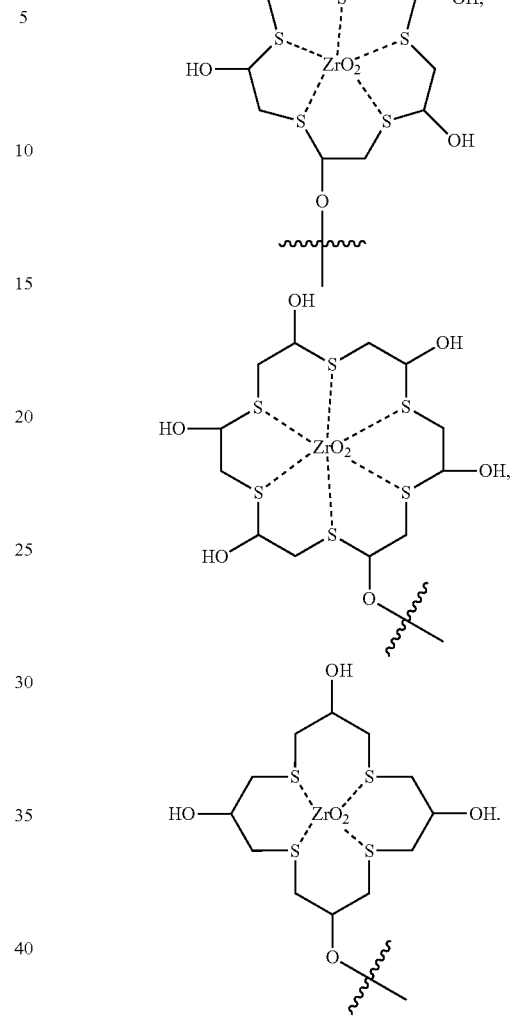
Non-limiting examples of compound of formula I are shown below:
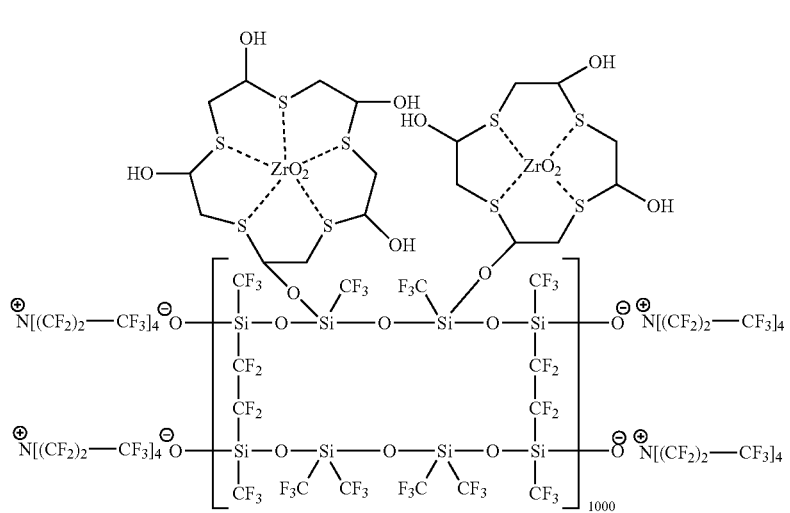
1

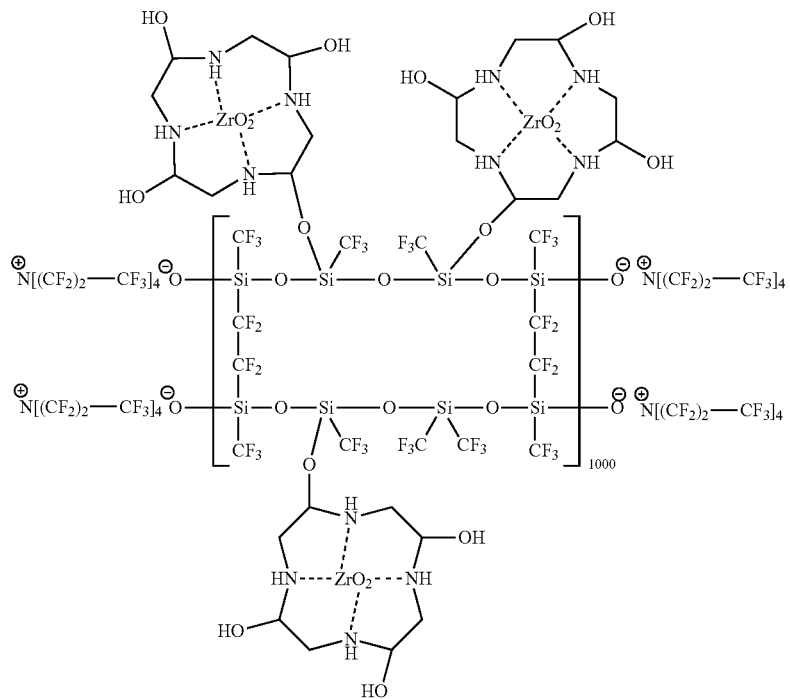
2
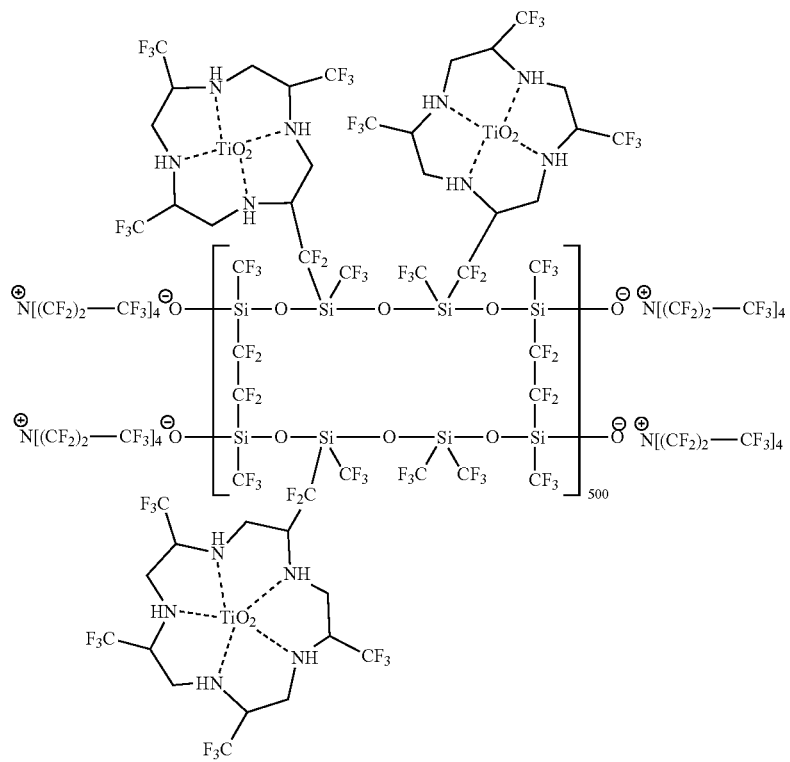
3

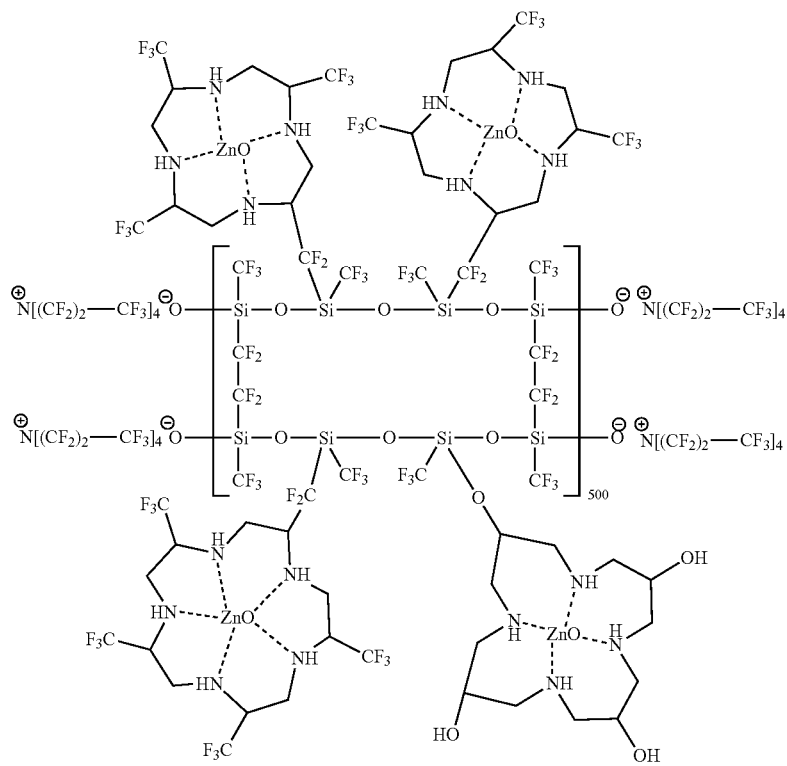

In some embodiments, a compound is of formula IV:

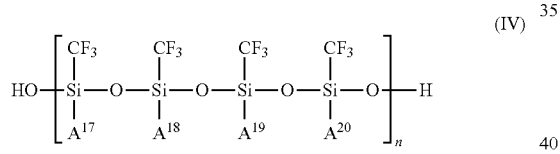

wherein n is an integer from 1 to 100; $A^{17}$ is a metal-aza crown complex or a metal-thio crown complex; $A^{18}$ is a metal-aza crown complex or a metal-thio crown complex; $A^{19}$ is a metal-aza crown complex or a metal-thio crown complex; and $A^{20}$ is a metal-aza crown complex or a metal-thio crown complex.

In some embodiments, each one of $A^{17}$-$A^{20}$ independently is a metal-thio crown complex. In some embodiments, each $A^{17}$-$A^{20}$ independently is a metal-aza crown complex. In some embodiments, $A^{17}$ and $A^{18}$ are metal-aza crown complexes, and $A^{19}$ and $A^{20}$ are metal-thio crown complexes.

In some embodiments, the metal-aza crown complex attached to compound of formula IV can be represented by:

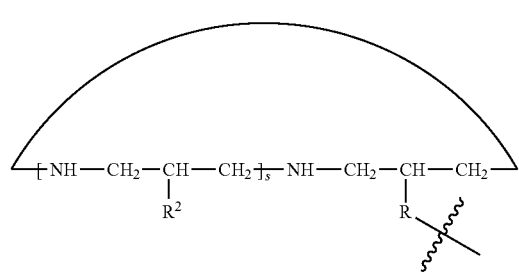

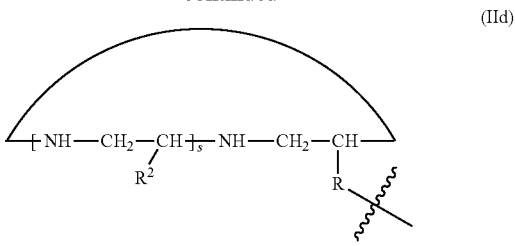

wherein s is an integer from 3 to 12; each R is independently, —O—, —$CF_2$—, —C(=O)—O—, —C(=O)—NH—, or —NH—; and each $R^2$ is independently, —H, —F, —$CF_3$, —OH, —$CF_2Cl$, or —$NH_2$. The metallic nanoparticle of the metal-aza crown complex may be a $ZrO_2$ nanoparticle, a $TiO_2$ nanoparticle, a ZnS nanoparticle, a ZnO nanoparticle, or any combination thereof.

In some embodiments, the metal-thio crown complex attached to compound of formula IV can be represented by:

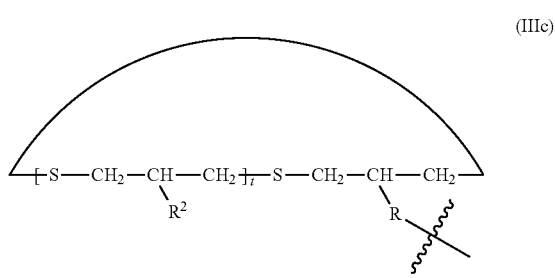

-continued

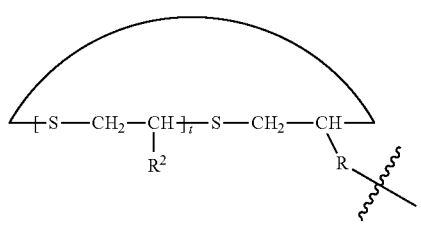
(IIId)

wherein t is an integer from 3 to 12; each R is, independently, —O—, —CF$_2$—, —C(=O)—O—, —C(=O)—NH—, or —NH—; and each R$^2$ is independently, —H, —F, —CF$_3$, —OH, —CF$_2$Cl, or —NH$_2$. The metallic nanoparticle of the metal-thio crown complex may be a ZrO$_2$ nanoparticle, a TiO$_2$ nanoparticle, a ZnS nanoparticle, a ZnO nanoparticle, or any combination thereof.

Non-limiting examples of compound of formula IV are shown below:

5

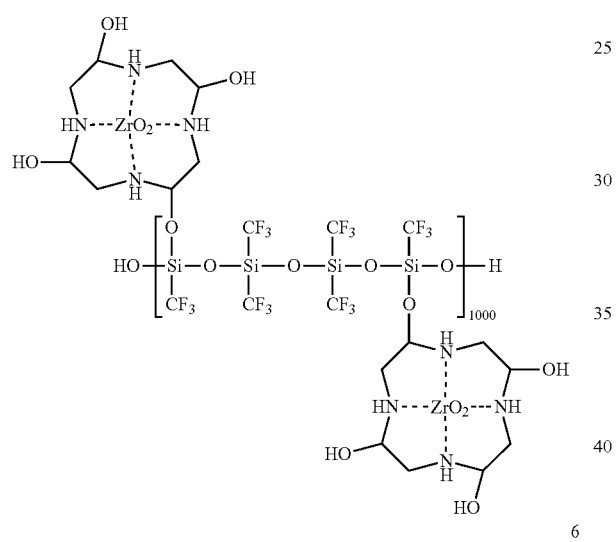

6

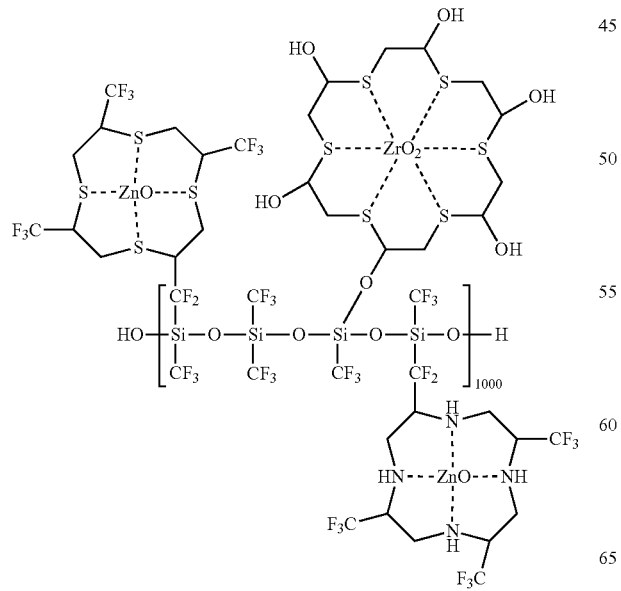

7

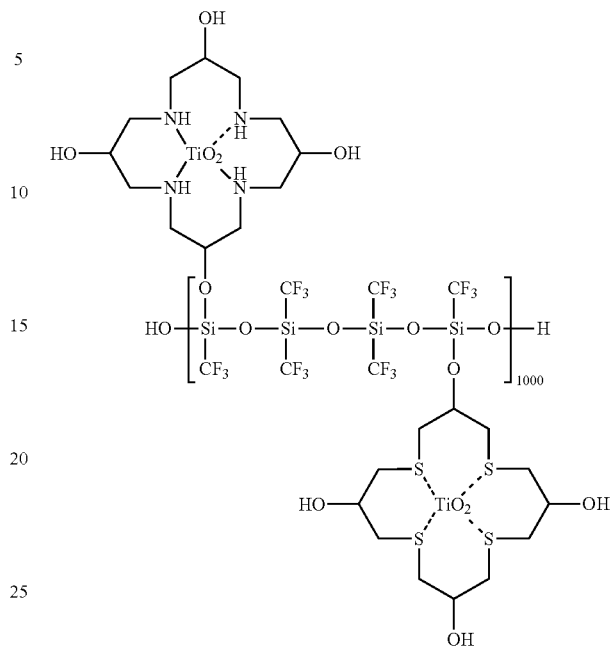

Also disclosed herein are novel aza-crown and thio-crown macromolecules. In some embodiments, a compound is of formula V:

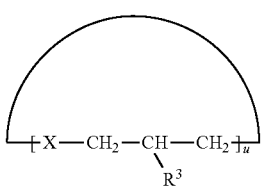
(V)

wherein X is —NH— or —S—; u is an integer from 4 to 12; and each R$^3$ is, independently, —H, —F, —Cl, —CF$_3$, —OH, —CF$_2$Cl, —CH$_2$Cl, —COCl, or —NH$_2$. In some embodiments, X is —NH—, and R$^3$ is, independently, —H, —F, —CF$_3$, —OH, —CF$_2$Cl, or —NH$_2$. In some embodiments, X is —S—, and R$^3$ is, independently, —H, —F, —CF$_3$, —OH, —CF$_2$Cl, or —NH$_2$.

Non-limiting examples of compound of formula V are shown below:

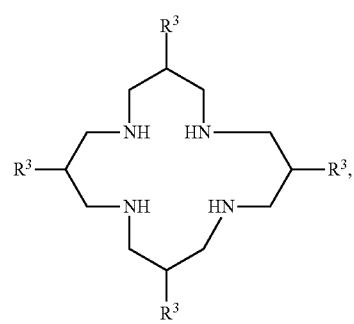

-continued

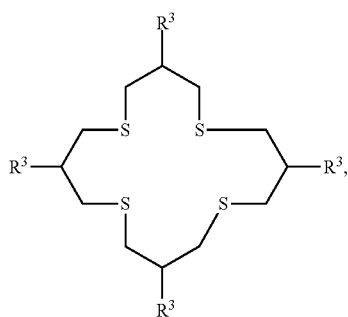

wherein each $R^3$ is, independently, —H, —F, —CF$_3$, —OH, —CF$_2$Cl, or —NH$_2$.

In some embodiments, a compound is of formula VI:

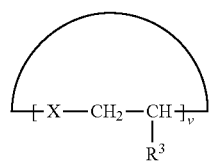

(VI)

wherein X is —NH— or —S—; v is an integer from 4 to 12; and each $R^3$ is, independently, —H, —F, —Cl, —CF$_3$, —OH, —CF$_2$Cl, —CH$_2$Cl, —COCl, or —NH$_2$. In some embodiments, X is —NH—, and $R^3$ is, independently, —H, —F, —CF$_3$, —OH, —CF$_2$Cl, or —NH$_2$. In some embodiments, X is —S—, and $R^3$ is, independently, —H, —F, —CF$_3$, —OH, —CF$_2$Cl, or —NH$_2$.

Non-limiting examples of compound of formula VI are shown below:

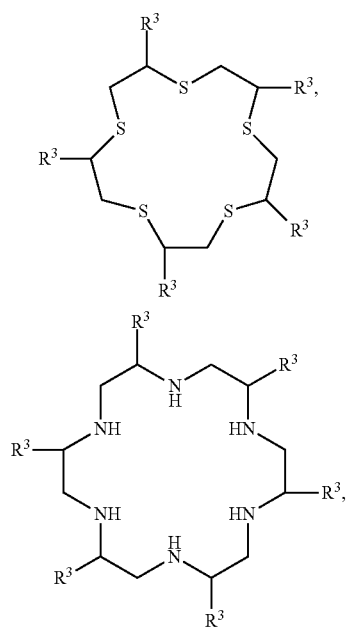

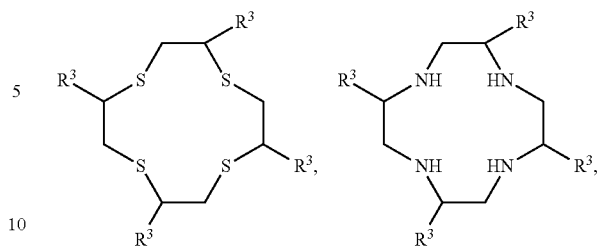

wherein each $R^3$ is, independently, —H, —F, —CF$_3$, —OH, —CF$_2$Cl, or —NH$_2$.

Also disclosed herein are methods to make compounds of formula I. In some embodiments, a method of making a siloxane compound of formula I may involve contacting a metal-crown complex with trifluorochloromethane and a silicon metal to form a dichlorosilane-trifluoromethyl-metal-crown complex, and hydrolyzing the dichlorosilane-trifluoromethyl-metal-crown complex to form a fluorinated siloxane polymer compound of formula IV, and contacting the polymer compound of formula IV with a bis-siloxane D4 compound and an anionic catalyst to form the siloxane compound of formula I.

An exemplary reaction is outlined below:

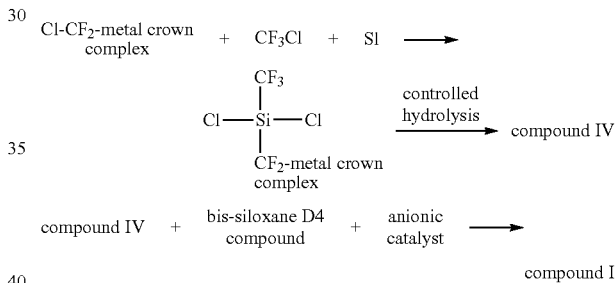

The metal-crown complex may be formed by contacting a crown macromolecule with a metallic nanoparticle, to form metal-aza crown complex or metal-thio crown complex. The metallic nanoparticle may be any metallic nanoparticle disclosed herein, such as a ZrO$_2$ nanoparticle, a TiO$_2$ nanoparticle, a ZnS nanoparticle, a ZnO nanoparticle, or any combination thereof. The crown macromolecule may be any aza-crown macromolecule or a thio-crown macromolecule described herein, and are represented by formulae V and VI.

In some embodiments, the metal-crown complex and the trifluoro-chloromethane may be contacted in a molar ratio of about 1:1 to about 1:4, about 1:1 to about 1:3, or about 1:1 to about 1:2. Specific examples include about 1:1, about 1:1.5, about 1:2.5, about 1:4, and ranges between any two of these values.

In some embodiments, the dichlorosilane-trifluoromethyl-metal-crown complex is subjected to a controlled hydrolysis step, resulting in the fluorinated siloxane polymer compound of formula IV. For example, hydrolysis may be controlled by varying the molar ratio of cyclic monomer to water.

In some embodiments, the bis-siloxane D4 compound may be represented by the structure:

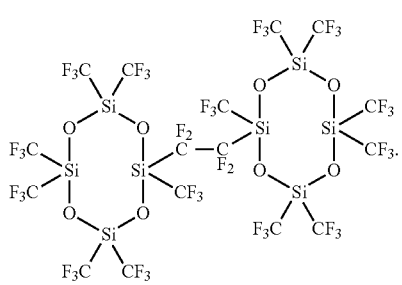

The anionic catalyst may be represented by the structure:

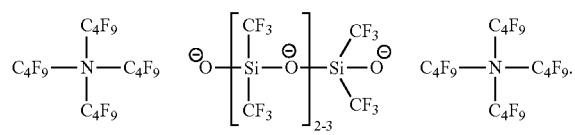

In some embodiments, the compound of formula IV and the bis-siloxane D4 compound are contacted in a molar ratio of about 1:0.1 to about 1:0.5, about 1:0.1 to about 1:0.4, or about 1:0.1 to about 1:0.2. Specific examples include about 1:0.1, about 1:0.2, about 1:0.3, about 1:0.4, about 1:0.5, and ranges between any two of these values.

Compounds of formula I may be considered to be a "living polymer network" because the tetrafluoroalkyl ammonium end groups may react with the network chains to restructure the crosslinks in the network. For example, when the polymer is subjected to temperatures above 300° C., the polymer active chain ends are transferred to Si—O—$C_4F_9$, and the catalyst is transferred to $N(C_4F_9)_3$ and siloxane oligomer, which is available at any time for further polymerization. While self-alignment occurs at such high temperatures via anionic polymerization, neither thermal degradation nor melting occurs. The presence of fluorine substituent groups in the catalyst and siloxane backbone increases the anionic initiation activity of both the catalyst and the monomer due to the high electro-negativity and electron withdrawing properties.

The compounds and polymers disclosed herein may have any or all of high thermal stability, good mechanical properties, self-healing properties, a low dielectric constant, and a low refractive index. Due to their high thermal stability, thermal degradation may not occur, or may be reduced compared to other compounds and polymers, during high temperature processing, for example, a solder reflow process in the manufacturing of optical circuits. Since the compounds and polymers are prepared by anionic living polymerization, they maintain the active catalyst, active polymerizable chain end, and cyclic structure in the system thereby meeting the fundamental requirements of being printable waveguide materials. Such compounds and polymers may be used in a wide variety of uses, including optical waveguides, tires, mechanical parts of a vehicle, sporting goods, coupling sockets, switches, printed wiring board pins, ice skating rinks, and the like.

The compounds and polymers disclosed herein may be used for preparing optical waveguides. An optical waveguide structure may have a light transmitting core material having a first refractive index, and a cladding material partially contacting or entirely surrounding the core material, wherein the cladding material has a second refractive index lower than the first refractive index of the core material, and wherein the core material includes one or more compounds of formula I, IV, V or VI.

The optical waveguides may be synthesized using any method known in the art. Briefly, a layer of cladding material is formed over a suitable substrate. The substrate may be any material upon which it is desired to establish a waveguide, such as a semiconductor material (silicon, silicon oxide, silicon oxide/silicon, gallium arsenide, silicon nitride, silica on silicon, or the like), glass, plastics, quartz, ceramics, or crystalline materials. The cladding material may be formed on the substrate by any known method, such as spin casting, dip coating, roller coating, doctor blading, or evaporating. Suitable cladding materials include silica xerogels, silicon oxide, metal oxides, air, silicon dioxide, benzocyclobutene, plasma oxides, acrylates, fluorinated acrylates, polyimides, and other polymers having a lower refractive index than the core. The siloxane core material can then be deposited into a thin film on top of the cladding. Before or after curing, the core siloxane material can optionally be patterned using known methods, such as photolithography, wet etching, reactive-ion etching (RIE), photoablation, and the like.

EXAMPLES

Example 1: Preparation of bis-siloxane D4 Compound

About 3 moles of hexafluorodimethyl dichlorosilane and 2 moles of trifluoromethyl-difluoromethyl dichlorosilane are mixed and subjected to controlled hydrolysis to obtain a fluorinated tetrasiloxane compound. The tetrasiloxane compound undergoes cyclization in the presence of zinc oxide to obtain a fluorinated cyclic siloxane (D4) monomer.

About 20 grams of above obtained cyclic siloxane (D4) monomer is mixed with 0.001 grams of the fully fluorinated benzoyl peroxide and heated at 120° C. for 30 minutes. The free radical coupling reaction takes place to form the bis-siloxane D4 compound.

Example 2: Preparation of Anionic Catalyst

About 0.1 mole of silicon metal is reacted with about 0.2 moles of trifluorochloromethane to obtain hexafluorodimethyl dichlorosilane. The hexafluorodimethyl dichlorosilane is subjected to controlled hydrolysis to obtain a hydroxyl terminated fluorinated tetrasiloxane compound. The tetrasiloxane compound undergoes cyclization in the presence of zinc oxide to form a fluorinated cyclic siloxane (D4) compound.

A reaction vessel is charged with 0.1 mole of fluorinated tetrabutyl-ammonium chloride that is prepared by reacting fluorinated tributylamine with fluorinated butyl chloride. The reaction vessel is cooled to 5° C., flushed with $N_2$, and about 0.05 mole of above obtained fluorinated cyclic siloxane (D4) monomer is added. The reaction is continued for one hour under $N_2$ atmosphere, and the product is purified and dried to obtain an anionic catalyst.

Example 3: Preparation of Metal-Aza Crown Complex

About 1 mole of epichlorohydrin is mixed with 1 mole of ammonia in the presence of 0.01 mole of sodium carbonate (catalyst) and 750 mL of acetonitrile (solvent). The mixture is heated to 25° C. for 180 minutes in an autoclave. Fractions are taken out every 30 minutes until the condensation reaction reaches the required molecular weight (degree of polymerization=4). The resulting product poly(2-hydroxy-3-iminopropylene) undergoes cyclisation reaction to form 12-crown-4 and 15-crown-5 aza-crown molecules. The aza-crown molecules are further incubated with $ZrO_2$ nanoparticles to obtain a metal-aza crown complexes.

The reaction is outlined below:

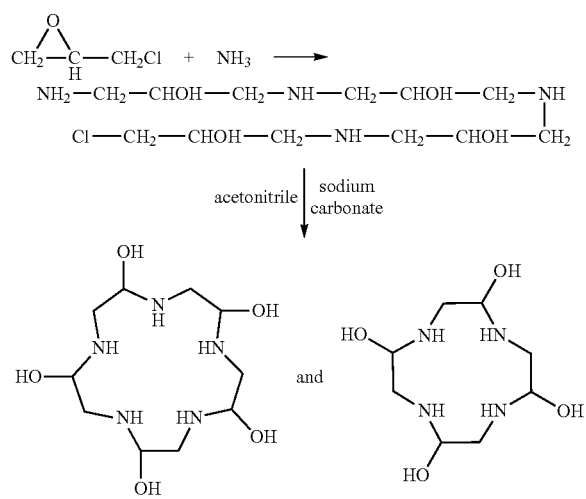

Example 4: Preparation of Compound 5

About 1 mole of metal-aza crown complex of Example 3 is mixed with 1 mole of trifluorochloromethane and 1 mole of silicon metal to form the methylated dichlorosilane-metal-crown complex. The methylated dichlorosilane-metal-crown complex is subdected to partial hydrolysis with a predetermined molar ratio of water at room temperature according to the chain length required to obtain compound 5.

Example 5: Preparation of Compound 2

About 1 mole of compound 5 is mixed with 0.1 mole of compound 8 in the presence of the anionic catalyst compound 9. The mixture is cooled to 0° C. for 40 minutes under a stream of nitrogen gas. The resulting polymer is a ladder type anionic living polysiloxane polymer compound 2. The degree of laddering can be controlled by the molar ratio of compound 1 and compound 8. The reaction can be carried out in aprotic solvents. It is to be noted that various polymeric compounds within the scope of formula I can be made by varying the starting material. For example compound 6 or compound 7 may be used in place of compound 5.

The polymer that is formed can be considered as a "living polymer network" as the active polymerizable chain end groups can react with the network chains to restructure the crosslinks in the network, giving the polymer its self-aligning property. In addition, the polymer may have high thermal stability, good mechanical properties, self-healing properties, a low dielectric constant, and a low refractive index.

Example 6: Preparation of a Waveguide

Planar waveguides are made on 3 inch (7.62 cm) silicon wafer substrates using the siloxane polymers of compounds 1-4 as the high refractive index core material, and silicon oxide as the cladding. The silicon oxide is spin-coated on a wafer to a thickness of about 1 μm. The core material (compounds 1-4) is then spun-onto the cladding film to a thickness of about 2 μm (6000 rpm for 100 seconds). Next, the samples are baked at 100° C. for 20 minutes and annealed at 150° C. As the siloxane polymers are expected to have high thermal stability, thermal degradation may not occur during subsequent high temperature processing, for example, a solder reflow process in the manufacturing of optical circuits containing the planar waveguides. The waveguide may also have good mechanical properties, self-healing properties, a low dielectric constant, and a low refractive index.

Example 7: An Article Prepared from Siloxane Polymers

The siloxane polymer pellets of compound 1 are heated in an injection molding machine and fed into a mold cavity and allowed to cool. The cooled polymer obtains the shape according to the contour of the cavity, and articles such as coupling sockets, switches, tennis rackets, and brake pads may be manufactured using appropriate molds. It will be expected that the articles manufactured from the siloxane polymer may have high thermal stability, good mechanical properties, self-healing properties, a low dielectric constant, and a low refractive index.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURES, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (example, bodies of the appended claims) are generally intended as "open" terms (example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound of formula I:

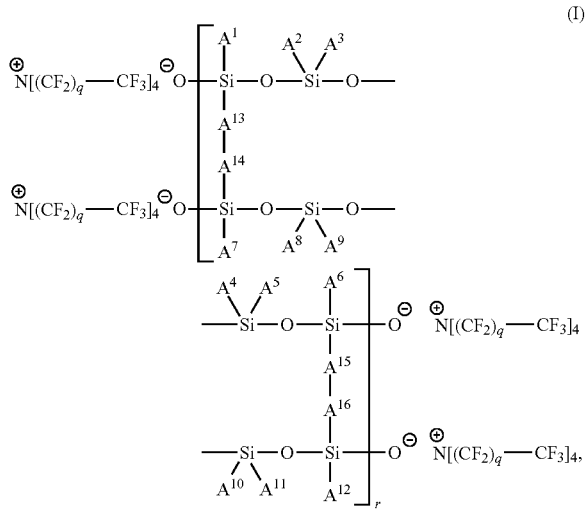

wherein
q is an integer from 1 to 3;
r is an integer from 1 to 10000;
each $A^1, A^2, A^3, A^4, A^5, A^6, A^7, A^8, A^9, A^{10}, A^{11}$, and $A^{12}$ independently is, —$CH_3$, substituted —$CH_3$, —$CH_2$—C(=O)—H, substituted —$CH_2$—C(=O)—H, —$C_6H_5$, substituted —$C_6H_5$, —CH=$CH_2$, substituted —CH=$CH_2$, —$CH_2$—CH=$CH_2$, substituted —CH$_2$—CH=CH$_2$, a metal-aza crown complex, a metal-thio crown complex, or a metal-acrylic acid complex, and wherein at least one of A$^1$, A$^2$, A$^3$, A$^4$, A$^5$, A$^6$, A$^7$, A$^8$, A$^9$, A$^{10}$, A$^{11}$, and A$^{12}$ is a metal-aza crown complex or a metal thio crown complex, wherein the metal-aza crown complex of the metal-thio crown complex comprises a metallic nanoparticle selected from a ZrO$_2$ nanoparticle, a TiO$_2$ nanoparticle, a ZnS nanoparticle, a ZnO nanoparticle, or any combination thereof complex; and each A$^{13}$, A$^{14}$, A$^{15}$, and A$^{16}$ independently is, —CH$_2$— or —CF$_2$—.

2. The compound of claim 1, wherein when any one of A$^1$ to A$^{12}$ is the metal-aza crown complex, the metal-aza crown complex comprises the metallic nanoparticle in contact with an aza crown molecule, and the aza crown molecule is selected from formula IIa or IIb:

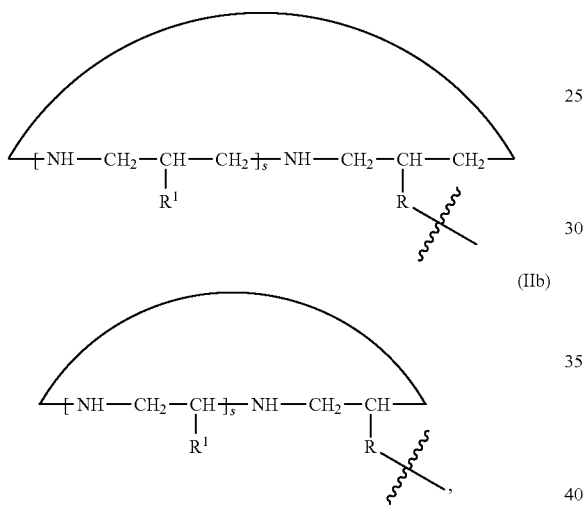

(IIa)

(IIb)

wherein
s is an integer from 3 to 12;
each R is independently, —O—, —CF$_2$—, —C(=O)—O—, —C(=O)—NH—, or —NH—; and
each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

3. The compound of claim 1, wherein when any one of A$^1$ to A$^{12}$ is the metal-thio crown complex, the metal-thio crown complex comprises a metallic nanoparticle in contact with a thio-crown molecule, and the thio-crown molecule is selected from formula IIIa or IIIb:

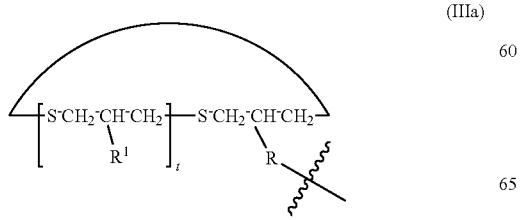

(IIIa)

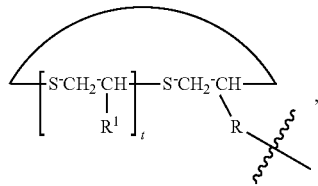

(IIIb)

wherein:
t is an integer from 3 to 12;
each R is independently, —O—, —CF$_2$—, —C(=O)—O—, —C(=O)—NH—, or —NH—; and
each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

4. The compound of claim 1, wherein the metal-aza crown complex is selected from:

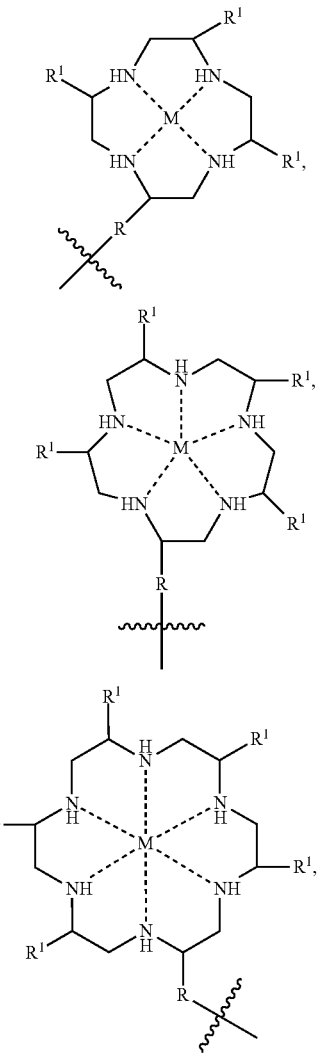

and

-continued

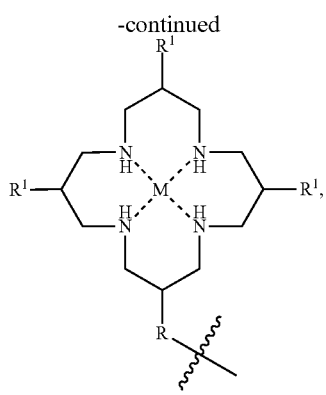

wherein:
M is ZrO$_2$ nanoparticle, TiO$_2$ nanoparticle, ZnS nanoparticle, or ZnO nanoparticle;
R is —O—, —CF$_2$—, —C(=O)—O—, —C(=O)—NH—, or —NH—; and
each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

5. The compound of claim 1, wherein the metal-thio crown complex is selected from:

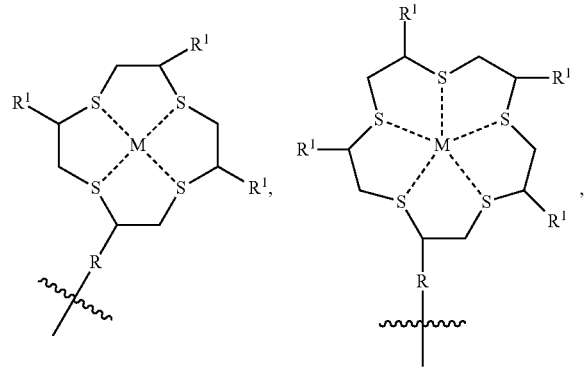

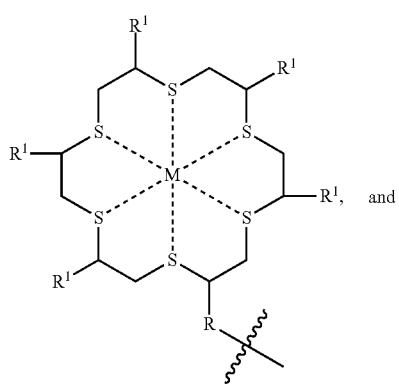

-continued

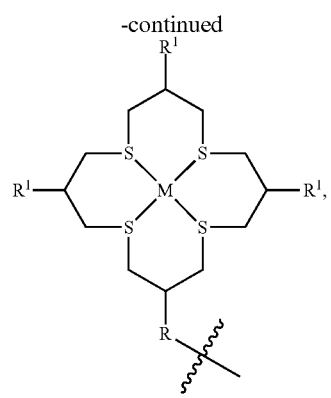

wherein:
M is ZrO$_2$ nanoparticle, TiO$_2$ nanoparticle, ZnS nanoparticle, or ZnO nanoparticle;
R is independently, —O—, —CF$_2$—, —C(=O)—O—, —C(=O)—NH—, or —NH—; and
each R$^1$ is independently, —H, —F, —CF$_3$, —OH, —CF$_2$Cl, —NH$_2$, a bivalent —O— linked to the siloxane polymer of formula I, a bivalent —CF$_2$— linked to the siloxane polymer of formula I, or a bivalent —NH— linked to the siloxane polymer of formula I.

6. A compound of formula IV:

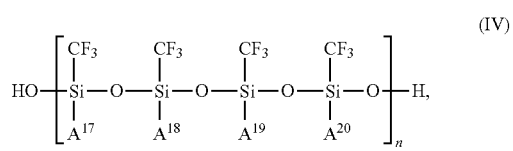

(IV)

wherein:
n is an integer from 1 to 100;
A$^{17}$ is a metal-aza crown complex or a metal-thio crown complex;
A$^{18}$ is a metal-aza crown complex or a metal-thio crown complex;
A$^{19}$ is a metal-aza crown complex or a metal-thio crown complex; and
A$^{20}$ is a metal-aza crown complex or a metal-thio crown complex.

7. The compound of claim 6, wherein when any one of A$^{17}$, A$^{18}$, A$^{19}$, or A$^{20}$ is the metal-aza crown complex, the metal-aza crown complex comprises a metallic nanoparticle in contact with an aza crown molecule, and the aza crown molecule is selected from formula IIc or IId:

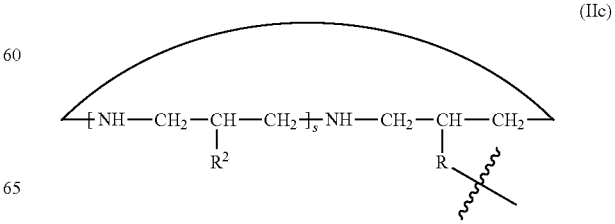

(IIc)

-continued

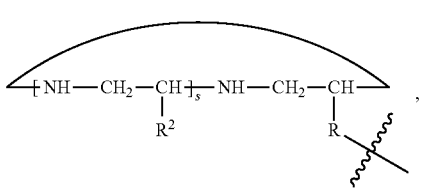
(IId)

wherein
s is an integer from 3 to 12;
each R is independently, —O—, —CF$_2$—, —C(=O)—O—, —C(=O)—NH—, or —NH—; and
each R$^2$ is independently, —H, —F, —CF$_3$, —OH, —CF$_2$Cl, or —NH$_2$.

8. The compound of claim 6, wherein when any one of A$^{17}$, A$^{18}$, A$^{19}$, or A$^{20}$ is the metal-thio crown complex, the metal-thio crown complex comprises a metallic nanoparticle in contact with a thio-crown molecule, and the thio-crown molecule is selected from formula IIIc or IIId:

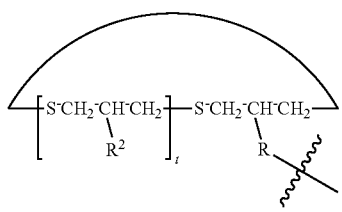
(IIIc)

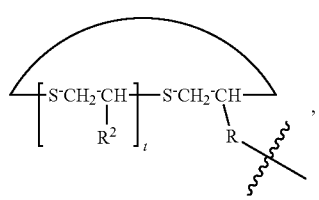
(IIId)

wherein:
t is an integer from 3 to 12;
each R is independently, —O—, —CF$_2$—, —C(=O)—O—, —C(=O)—NH—, or —NH—; and
each R$^2$ is independently, —H, —F, —CF$_3$, —OH, —CF$_2$Cl, or —NH$_2$.

9. The compound of claim 7, wherein the metallic nanoparticle is a ZrO$_2$ nanoparticle, a TiO$_2$ nanoparticle, a ZnS nanoparticle, a ZnO nanoparticle, or any combination thereof.

10. An optical waveguide structure comprising:
a light transmitting core material having a first refractive index; and
a cladding material partially contacting or entirely surrounding the light transmitting core material, wherein the cladding material has a second refractive index lower than the first refractive index of the light transmitting core material, and wherein the light transmitting core material comprises one or more compounds of formula I

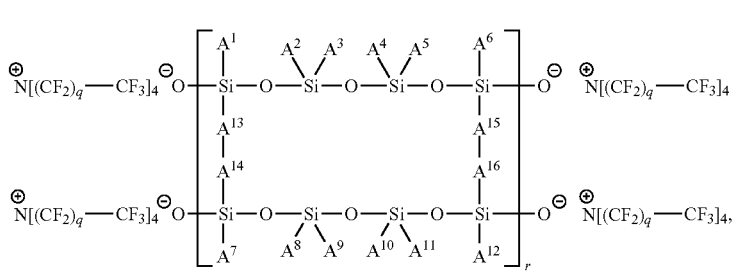
(I)

wherein:
q is an integer from 1 to 3;
r is an integer from 1 to 10000;
each A$^1$, A$^2$, A$^3$, A$^4$, A$^5$, A$^6$, A$^7$, A$^8$, A$^9$, A$^{10}$, A$^{11}$, and A$^{12}$ independently is, —CH$_3$, substituted —CH$_3$, —CH$_2$—C(=O)—H, substituted —CH$_2$—C(=O)—H, —C$_6$H$_5$, substituted —C$_6$H$_5$, —CH=CH$_2$, substituted —CH=CH$_2$, —CH$_2$—CH=CH$_2$, substituted —CH$_2$—CH=CH$_2$, a metal-aza crown complex, a metal-thio crown complex, or a metal-acrylic acid complex, and wherein at least one of A$^1$, A$^2$, A$^3$, A$^4$, A$^5$, A$^6$, A$^7$, A$^8$, A$^9$, A$^{10}$, A$^{11}$, and A$^{12}$ is a metal-aza crown complex or a metal-thio crown complex; and
each A$^{13}$, A$^{14}$, A$^{15}$, and A$^{16}$ independently is —CH$_2$— or —CF$_2$—.

11. A method to make a siloxane compound of formula I, the method comprising:
contacting a metal-crown complex with trifluorochloromethane and a silicon metal to form a dichlorosilane-trifluoromethyl-metal-crown complex;
hydrolyzing the dichlorosilane-trifluoromethyl-metal-crown complex to form a fluorinated siloxane polymer compound of formula IV

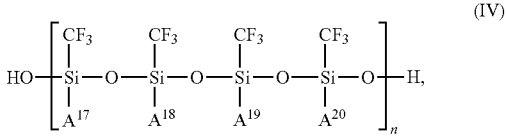
(IV)

wherein:
n is an integer from 1 to 100,
A$^{17}$ is a metal-aza crown complex or a metal-thio crown complex,
A$^{18}$ is a metal-aza crown complex or a metal-thio crown complex, A$^{19}$ is a metal-aza crown complex or a metal-thio crown complex, and A$^{20}$ is a metal-aza crown complex or a metal-thio crown complex; and contacting the fluorinated siloxane polymer compound of formula IV with a bis-siloxane D4 compound

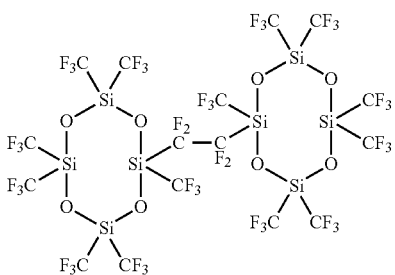

and an anionic catalyst to form the siloxane compound of formula I

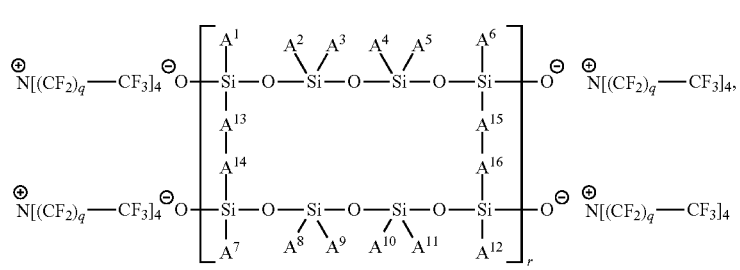

wherein q is an integer from 1 to 3;

r is an integer from 1 to 10000;

each A$^1$, A$^2$, A$^3$, A$^4$, A$^5$, A$^6$, A$^7$, A$^8$, A$^9$, A$^{10}$, A$^{11}$, and A$^{12}$ independently is, —CH$_3$, substituted —CH$_3$, —CH$_2$—C(=O)—H, substituted —CH$_2$—C(=O)—H, —C$_6$H$_5$, substituted —C$_6$H$_5$, —CH=CH$_2$, substituted —CH=CH$_2$, —CH$_2$—CH=CH$_2$, substituted —CH$_2$—CH=CH$_2$, a metal-aza crown complex, a metal-thio crown complex, or a metal-acrylic acid complex, and wherein at least one of A$^1$, A$^2$, A$^3$, A$^4$, A$^5$, A$^6$, A$^7$, A$^8$, A$^9$, A$^{10}$, A$^{11}$, and A$^{12}$ is a metal-aza crown complex or a metal-thio crown complex; and each A$^{13}$, A$^{14}$, A$^{15}$, and A$^{16}$ independently is —CH$_2$— or —CF$_2$—.

12. The method of claim 11, wherein the dichlorosilane-trifluoromethyl-metal-crown complex is formed by contacting a crown macromolecule with a metallic nanoparticle, the crown macromolecule represented by the formula V or VI:

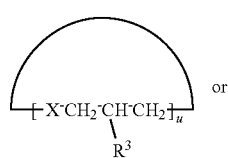

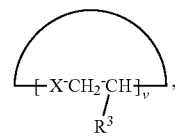

wherein:
each X is —NH— or —S—;
u is an integer from 4 to 12;
v is an integer from 4 to 12; and
each R$^3$ is independently, —F, —CF$_3$, —OH, —CF$_2$Cl, —CH$_2$Cl, —COCl, or —NH$_2$.

13. The method of claim 12, wherein the metallic nanoparticle is a ZrO$_2$ nanoparticle, a TiO$_2$ nanoparticle, a ZnS nanoparticle, a ZnO nanoparticle, or any combination thereof.

14. The method of claim 11, wherein hydrolyzing the dichlorosilane-trifluoromethyl-metal-crown complex comprises controlled hydrolysis of the dichlorosilane-trifluoromethyl-metal-crown complex.

15. The method of claim 11, wherein contacting the fluorinated siloxane polymer compound of formula IV comprises contacting with an anionic catalyst including:

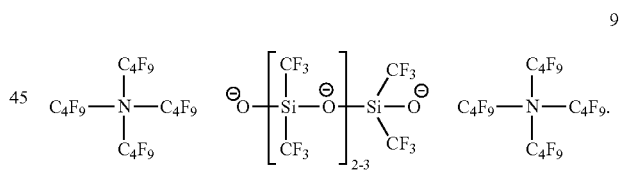

16. The method of claim 11, wherein contacting the metal-crown complex and the trifluorochloromethane comprises contacting at a molar ratio of about 1:1 to about 1:4.

17. The method of claim 11, wherein contacting the fluorinated siloxane polymer compound of formula IV and the bis-siloxane D4 compound comprises contacting at a molar ratio of about 1:0.1 to about 1:0.5.

18. The compound of claim 8, wherein the metallic nanoparticle is a ZrO$_2$ nanoparticle, a TiO$_2$ nanoparticle, a ZnS nanoparticle, a ZnO nanoparticle, or any combination thereof.

19. The optical waveguide structure of claim 10, further comprising a substrate in contact with the light transmitting core material.

20. The optical waveguide structure of claim 19, wherein the substrate is selected from the group consisting of silicon, silicon oxide, silicon oxide/silicon, gallium arsenide, silicon nitride, silica on silicon, glass, plastic, quartz, ceramic, and crystalline material.

21. The optical waveguide structure of claim 10, wherein the cladding material is selected from the group consisting of silica xerogels, silicon oxide, metal oxides, air, silicon dioxide, benzocyclobutene, plasma oxides, acrylates, fluorinated acrylates, polyimides.

* * * * *

UNITED STATES PATENT AND TRADEMARK OFFICE
CERTIFICATE OF CORRECTION

PATENT NO. : 9,994,597 B2
APPLICATION NO. : 15/306471
DATED : June 12, 2018
INVENTOR(S) : Sjong et al.

It is certified that error appears in the above-identified patent and that said Letters Patent is hereby corrected as shown below:

In the Specification

In Column 1, Line 10, please delete "2016" and insert -- 2014 -- therefor.

In Column 21, Lines 15-24, please delete

"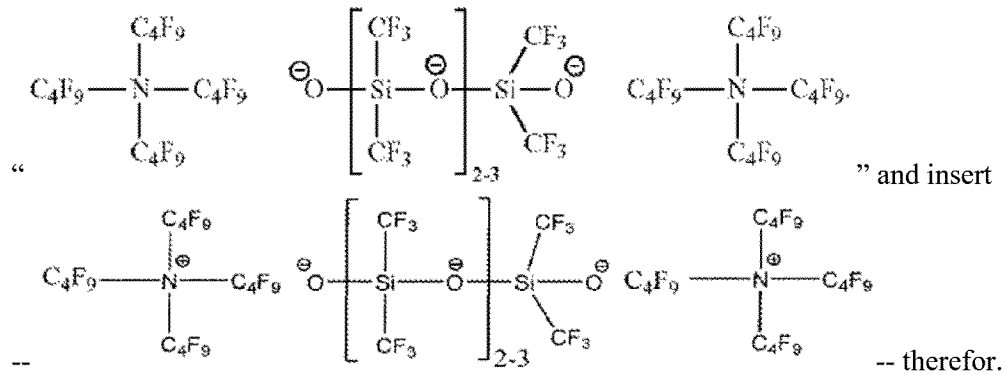 " and insert

-- -- therefor.

In Column 26, Line 60, please delete "wherein" and insert -- wherein: -- therefor.

In Column 27, Line 6, please delete "metal-aza crown complex of the metal-thio" and insert -- metal-aza crown complex or the metal-thio -- therefor.

In Column 27, Line 10, please delete "thereof complex; and" and insert -- thereof; and -- therefor.

In Column 27, Line 42, please delete "wherein" and insert -- wherein: -- therefor.

In Column 27, Line 53, please delete "comprises a" and insert -- comprises the -- therefor.

In Column 32, Line 5, please delete "structure comprising" and insert -- structure, comprising -- therefor.

Signed and Sealed this
Twenty-second Day of August, 2023

Katherine Kelly Vidal
*Director of the United States Patent and Trademark Office*

CERTIFICATE OF CORRECTION (continued)

In Column 32, Line 43, please delete "independently is" and insert -- independently is, -- therefor.

In Column 33, Line 38, please delete "wherein" and insert -- wherein: -- therefor.

In Column 33, Line 52, please delete "independently is" and insert -- independently is, -- therefor.

In Column 34, Line 13, please delete "-F, -CF₃, -OH" and insert -- -F, -Cl, -CF3, -OH -- therefor.

In Column 34, Lines 43-47, please delete

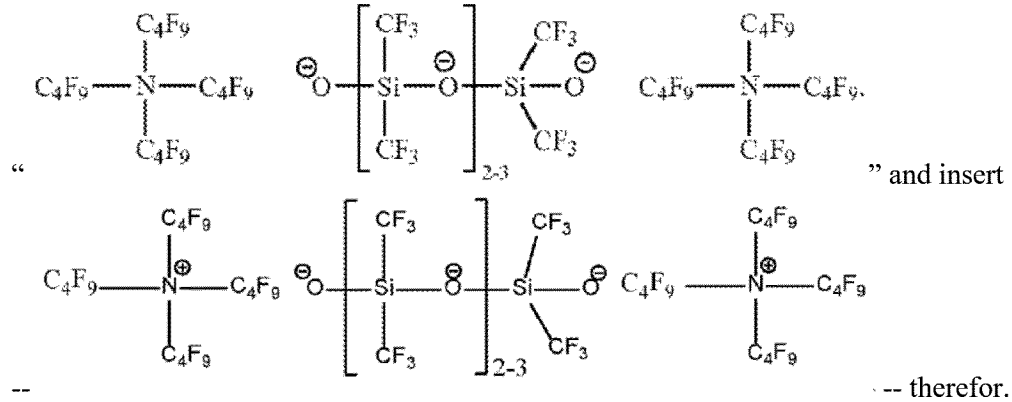

In Column 34, Line 42, please delete "9" in the righthand column therefor.